United States Patent [19]

Scannell

[11] Patent Number: 5,198,576
[45] Date of Patent: Mar. 30, 1993

[54] BICYCLOOCTYL PHOSPHINES AND CATALYSTS THEREOF

[75] Inventor: Ralph T. Scannell, Baton Rouge, La.

[73] Assignee: Ethyl Corporation, Richmond, Va.

[21] Appl. No.: 749,724

[22] Filed: Aug. 26, 1991

[51] Int. Cl.$^5$ ............... C07C 63/04; C07F 15/00; C07F 15/02
[52] U.S. Cl. .................................. 562/493; 556/21; 556/136; 556/146
[58] Field of Search ............... 562/493; 556/21, 136, 556/146

[56] References Cited

U.S. PATENT DOCUMENTS

| | | | |
|---|---|---|---|
| 3,748,332 | 7/1973 | Wilkinson | 260/270 R |
| 3,793,355 | 2/1974 | Wilkinson | 260/429 R |
| 3,878,122 | 4/1975 | Pennella | 252/411 R |
| 4,268,454 | 5/1981 | Pez et al. | 260/439 R |
| 4,440,936 | 4/1984 | Riley | 562/433 |
| 4,506,030 | 3/1985 | Jones | 502/155 |
| 4,604,447 | 8/1986 | Kumobayashi et al. | 556/7 |
| 4,605,750 | 8/1986 | Kumobayashi et al. | 556/7 |
| 4,691,037 | 9/1987 | Yoshikawa et al. | 556/18 |

OTHER PUBLICATIONS

Krenzfeld et al. React. Kinet. Catal. Lett., 24(1–2), 153–6 (1984).

*Primary Examiner*—José G. Dees
*Assistant Examiner*—Joseph M. Conrad, III
*Attorney, Agent, or Firm*—Richard J. Hammond

[57] ABSTRACT

Bicyclooctyl phosphines are disclosed having the formula:

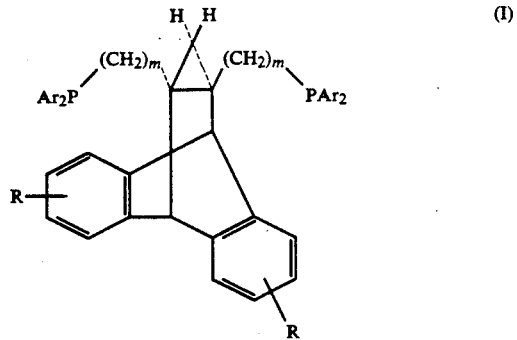

where R is $C_1$ to $C_6$ linear or branched alkyl, phenyl, substituted phenyl, halo, or $C_1$ or $C_6$ alkoxy; Ar is phenyl, substituted phenyl, naphthyl or substituted naphthyl; and x is 0 or 1.

These phosphines are treated with ruthenium compounds to form a complex of the formula $Ru_xH_yCl_z$ (anthraphos-m)$_2$ (S)$_p$, where S is a tertiary amine; and when y is 0, then x is 2, z is 4 and p is 1; and when y is 1, then x is 1, z is 1 and p is 0; where anthraphos-m is:

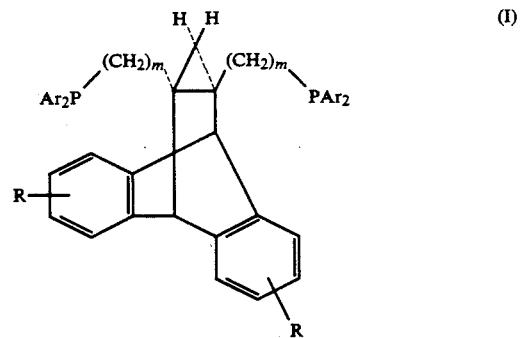

where R is $C_1$ to $C_6$ linear or branched alkyl, phenyl, substituted phenyl, $C_1$ to $C_6$ linear or branched alkoxy or halo; Ar is phenyl or substituted phenyl or naphthyl or substituted naphthyl; and m is 0 or 1.

The complex is useful in a process for the asymmetric reduction of olefinic carboxylic acids of the formula:

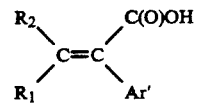

where $R_1$ and $R_2$ are the same or different and are hydrogen, alkyl, cycloalkyl or haloalkyl; and Ar' is aryl or substituted aryl.

14 Claims, No Drawings

BICYCLOOCTYL PHOSPHINES AND CATALYSTS THEREOF

FIELD OF INVENTION

This invention relates to certain bicyclooctyl phosphines, to the ruthenium complexes thereof and to a process for the catalytic reduction of aromatic-substituted olefinic carboxylic acids. More specifically, this invention relates to aromatic substituted bicyclooctane phosphines, the ruthenium complexes thereof and a process for asymmetrically, catalytically reducing aromatic-substituted olefinic carboxylic acids using said complex or a mixture of a ruthenium compound and the optically active form of the bicyclooctyl phosphine.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, appropriate chirality, a structure capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., *Tetrahedron*, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos.: 4,691,037; 4,739,084; 4,739,085; 4,764,629; 4,994,607; and 4,766,227. Unlike the more classical models of chiral (asymmetric) molecules, chirality in the case of the BINAP compounds arises from the restricted rotation about the single bond joining the naphthalene rings. Isomers arising from this type of asymmetry are termed atropisomers.

BINAP-based Ru(II) and Rh(I) complexes induce high enantioselectivity in catalytic reactions. See Noyori and Takaya, *Acc. Chem. Res.*, 1990, 23, 345.

The BINAP ruthenium complexes are dramatically different than the rhodium ones. They have been used to catalyze a variety of asymmetric hydrogenations, including the hydrogenation of enamides and alkyl and aryl-substituted acrylic acids. See Noyori, et al., *Modern Synthetic Methods*, 1989, 5, 115, incorporated herein by reference. Unlike the rhodium catalyzed reductions, ruthenium(II) carboxylate complexes possessing the BINAP ligand are efficient catalysts for the enantioselective hydrogenation of α,β-unsaturated carboxylic acids. According to Ohta, et al, *J. Org. Chem*, 52, 3174 (1982), the carboxyl moiety of the substrate, and not other oxygen containing groups, is responsible for the stereoselective reaction. Asymmetric reductions of noncarboxyl-containing substrates by ruthenium complexes are inefficient.

The preparation of the BINAP-bearing ruthenium complexes, while not only sophisticated, is time consuming and expensive. Accordingly, it would be advantageous to be able to carry out these enantioselective transformations using more readily prepared catalysts.

In rhodium catalyzed asymmetric reactions in situ methods of preparing the active catalysts are well established. Enantiomers of trans-11,12-bis-(diphenylphosphenomethyl)-9,10-dihydro-9,10-etanoanthracene (anthraphos) were treated with cyclooctadienerhodium chloride and used to asymmetrically reduce cinnamic and itaconic acids. See Kreuzfeld et al., *React. Kenet. Catal. Lett.* 24 (1-2) 157-60 (1984) and Döbler et al., *J. f. prakt. Chemie*, 325 (6) 1021-26 (1983), incorporated herein by reference. However, the use of ruthenium with these cyclic phosphines has never been reported.

SUMMARY OF THE INVENTION

The present invention involves a novel method for the use of organoruthenium compounds which, when admixed in an appropriate solvent with ligands having optical activity, can be used as an in situ generated catalyst to effect the asymmetric reduction of certain unsaturated organic compounds.

DESCRIPTION OF THE PREFERRED EMBODIMENTS

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl.

Cycloalkyl means cyclic alkyl having 3 to 7 carbon atoms and includes cyclopropyl, cyclobutyl, cyclopentyl, cyclohexyl and cycloheptyl.

Aryl means phenyl or naphthyl.

Substituted aryl means phenyl or naphthyl substituted by at least one substituent selected from the group consisting of halogen (chlorine, bromine, fluorine or iodine), amino, nitro, hydroxy, alkyl, alkoxy, which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Haloalkyl means straight or branched chain alkyl having 1 to 10 carbon atoms which is substituted by at least one halogen as mentioned above.

Phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl.

Substituted phenylalkyl means above-mentioned phenylalkyl which is substituted by at least one substituent selected from the group consisting of halogen, amino, nitro, hydroxy, alkyl, alkoxy and haloalkyl on the phenyl nucleus.

The bicyclic compounds of use in the process of the present invention have the following formula

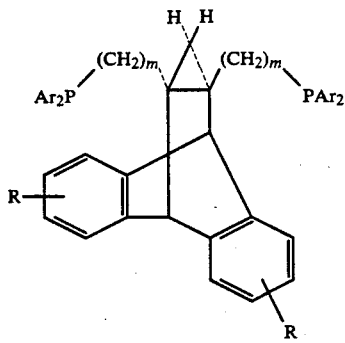

where R is $C_1$ to $C_6$ linear or branched alkyl, phenyl, substituted phenyl, $C_1$ to $C_6$ linear or branched alkoxy or halo, Ar is phenyl or substituted phenyl or naphthyl or substituted naphthyl and m is 0 or 1.

The term "anthraphos-m" is also used to identify these compounds, "m" being the integer in the number of methylene groups attached to the phosphorous atom in the above compounds of formula I, e.g., m=1 or 0 is anthraphos-1 or anthraphos-0.

The compounds of formula I where m is 1 and R is hydrogen, anthraphos-1, are known in the prior art. Their method of preparation (starting with the Diels-Alder reaction product of fumaric acid and anthracene) is disclosed in Döbler et al., *J. f. prakt. Chemie* 325 (6) 1025-26 (1983) and incorporated herein by reference.

In preparing the compounds of formula 1 where m=0 and R is hydrogen (anthraphos-0), the most convenient route for the preparation starts with the Diels-Alder reaction of anthracene with vinylene carbonate to form compounds of the following formula

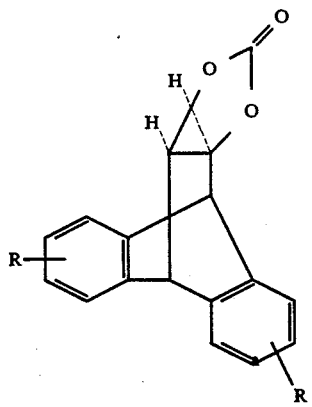

where R is as previously defined. The cyclic carbonate of formula II is easily hydrolyzed to the cis-diol (using, for example, aqueous base) followed by oxidation (to yield the dione) and lithium aluminum hydride reduction to form the trans diol. Derivatizing with d-(+)-camphano-sulfonic acid produces the readily resolved disulfonate ester of the following formula:

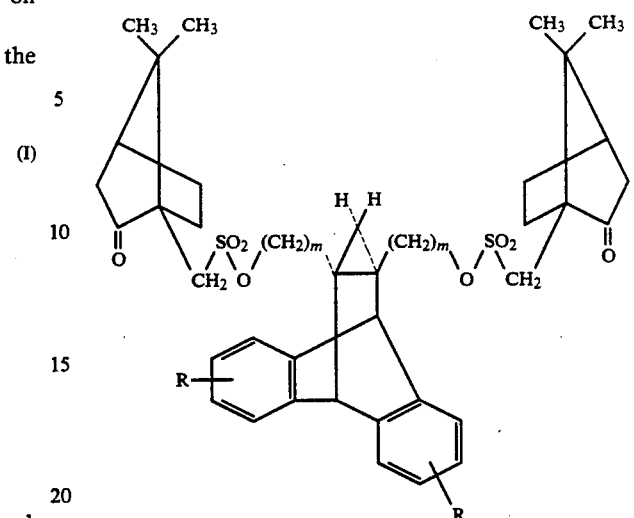

Displacement of the camphor sulfonyl group with diarylphosphide anion yields the desired compounds of formula I where m is 0. The reactions of these functional groups are well known. See, for example, J. March, *Advanced Organic Chemistry*, John Wiley & Sons, New York, N.Y., 3d edition, 1985, under the appropriate reaction types, incorporated herein by reference.

The enantioselective preparations of the present invention are carried out using α-aryl olefinic carboxylic acids.

The olefinic carboxylic acids have the formula:

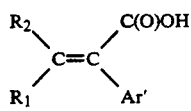

where $R_1$ and $R_2$ are the same or different and are hydrogen, alkyl, cycloalkyl, or haloalkyl and Ar' is aryl or substituted aryl. Preferably $R_1$ and $R_2$ are the same or different and are hydrogen or alkyl. Most preferred in the above carboxylic acids is where $R_1$ and $R_2$ are the same and are hydrogen or methyl. They are reduced (hydrogenated) asymmetrically by a catalytic process employing a mixture of (i) a ruthenium compound and (ii) the optically active compounds of formula I. It is not necessary to isolate the chiral metal catalyst that may be formed in this mixture prior to hydrogenation of the substrate.

The ruthenium compounds of use in this invention may be any of a wide variety of ruthenium-containing materials and include, for example, the halides such as ruthenium(III) bromide or ruthenium(III) chloride, mixed halide-chelate complexes such as (cycloocta-1,5-diene)ruthenium(II) chloride polymer, i.e., the chelate complex salts such as illustrated by $[Ru(COD)Cl_2]_n$, or (cycloocta-1,5-diene)ruthenium(II) (2,4-pentanedionate) or ruthenium(III) (2,4-pentanedionate). Interestingly, the present invention can be successfully carried out when starting with either Ru(II) or Ru(III) complexes whereas prior art discloses that the only effective catalysts are those from the Ru(II) species.

The preferred ruthenium compounds of use in the process of the present invention are the chelate complexes of the formula:

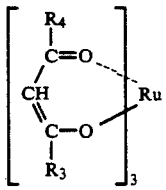

where $R_3$ and $R_4$ are the same or different and are alkyl, aryl, haloalkyl, phenylalkyl or substituted phenylalkyl.

In the preferred ruthenium compounds, it is most preferred that $R_3$ and $R_4$ are the same and are alkyl of 1 to 12 carbon atoms having a linear or branched chain. Particularly preferred are where $R_3$ and $R_4$ are the same and are linear or branched $C_1$ to $C_6$ alkyl group. Illustrative alkyl groups most preferably employed as $R_3$ and $R_4$ are methyl, ethyl, propyl, isopropyl, butyl, isobutyl, secondary butyl, tertiary butyl, pentyl, isopentyl, neopentyl, trifluoromethyl and the like.

The asymmetric catalytic hydrogenations utilizing the catalyst mixture of (i) and (ii) above is mixed with a solution of an α-aryl olefinic carboxylic acid, typically in a molar ratio of (i):(ii) of 10:1 to 1:10, preferably 8:1 to 1:8, most preferably 1:1.

The molar ratio of (i) to the olefinic carboxylic acid is between about 1 to 20 to about 1 to 20,000, preferably about 1 to 100 to about 1 to 10,000, most preferably about 1 to 5,000 to about 1 to 10,000.

The combination of the catalyst mixture, the olefinic carboxylic acid and suitable organic solvent, provide a system suitable for hydrogenation at elevated hydrogen pressure, i.e., pressures above about 75 psig.

To achieve enantioselective hydrogenation of the α-aryl olefinic carboxylic acid, a mixture of (i) and (ii) in the hydrogenation solvent must be given time (typically 1 to 5 hours) to become activated, either with or without hydrogen pressure at room temperature or at elevated temperature, before the substrate is introduced.

While the preferred methods for carrying out this reduction of the olefinic carboxylic acids is by the in situ generation of the catalytic species, it is also possible to prepare the catalyst prior to addition to the reaction mass. As such, the final catalyst has the formula:

$Ru_xH_yCl_z(anthraphos\text{-}m)_2 (S)_p$ (III)

where S is a tertiary amine; and when y is 0, then x is 2, z is 4 and p is 1; and when y is 1, then x is 1, z is 1 and p is 0; where anthraphos-m is:

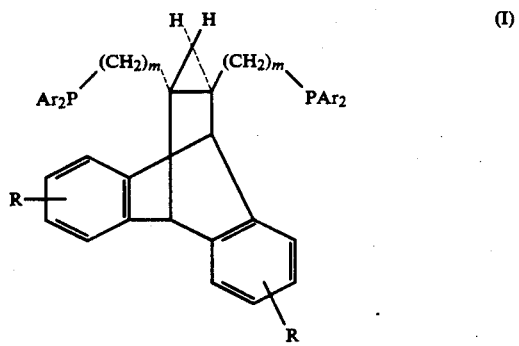

Examples of the tertiary amine for the compound S include triethylamine, tri-n-butylamine, tri-n-octylamine, N-methylpiperidine, N-methylpyrrolidine, N-methylmorpholine, pyridine, dimethylaniline and tetramethylethylenediamine.

The ruthenium-optically active phosphine complex of formula III can be obtained by the methods described in T. Ikariya et al., *J. Chem. Soc. Chem. Commun.*, pp. 922–924 (1985) and European Patent No. 174,057A. That is, in the case of y=0, ruthenium chloride is reacted with cycloocta-1,5-diene (abbreviated as "COD") in an ethanol solution to form $[RuCl_2(COD)]_n$, and one mole of this complex is reacted with 1.2 moles of anthraphos-m under heating in a solvent such as toluene or ethanol in the presence of 4 moles of a tertiary amine such as triethylamine.

Further, in the case of y=1, one mole of $[RuCl_2(COD)]_n$ is reacted with 2.25 moles of anthraphos-m and 4.5 moles of tertiary amine.

If an optically active form of anthraphos-m is used in the above-described method, a ruthenium-phosphine complex having corresponding optically active properties is obtained.

Specific examples of the ruthenium-optically active phosphine complex are listed below:

$Ru_2Cl_4(anthraphos\text{-}0)_2(NEt_3)$;
$Ru_2Cl_4(anthraphos\text{-}1)_2(NEt_3)$;
$RuHCl(anthraphos\text{-}0)_2$;
$RuHCl(anthraphos\text{-}1)_2$;
$Ru_2Cl_4(phenyl\text{-}anthraphos\text{-}0)_2(NEt_3)$ (where R=phenyl)
$Ru_2Cl_4(anthraphos\text{-}1)_2(NBu_3)$; and
$Ru_2Cl_4[(-)\text{-}anthraphos\text{-}1]_2$

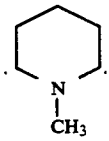

The compounds of formula III are admixed with the olefinic carboxylic acids in a ratio of between about 1 to 20 to about 1 to 20,000, preferably about 1 to 100 to about 1 to 10,000, most preferably about 1 to 5,000 to about 1 to 10,000, catalyst to acid. Times, temperatures and pressures are similar to that described earlier for in situ hydrogenations.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Methods (General)

All solvents used in the hydrogenation were reagent grade and were purged with nitrogen for at least 2 hours to remove oxygen. Conversions were determined by GC (area %); optical purities were determined by HPLC using a chiral column. The metal reactors used were constructed of Monel 400.

Preparation of (Anthraphos-m)Ruthenium(II)Diacetate

The materials were made by the method of Kreuzfeld et al., React. Kenet. Catal. Lett., 24(1-2), pp. 157-60, (1988).

EXAMPLE 1

The starting ruthenium(III) (2,4-pentanedionate) and anthraphos-1 were weighed and combined in a 25 ml flask in a nitrogen-filled glove box. The mixture was transferred to the high pressure reactor using 30 ml of methanol. The reactor was flushed with hydrogen ($3 \times 300$ psi), warmed to 60° C. and then stirred at 1000 psi ($H_2$) for 3 hr. The reactor was cooled to ambient temperature and then vented. A solution of 2-(4isobutylphenyl)acrylic acid (UA) in 10 ml of methanol was added to the reactor. After flushing ($3 \times 300$ psi $H_2$) and sealing the vessel under 1000 psi hydrogen, the mixture was stirred (600 rpm) and sampled for GC analyses as shown in the Table. After 3 hours at 24° C., the hydrogenation was complete. The saturated amide product was hydrolyzed to ibuprofen as described below. The optical purity of the S-ibuprofen hydrolysis product was 67% by HPLC.

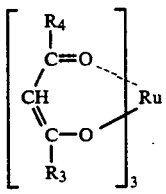

where $R_3$ and $R_4$ are the same or different and are alkyl, haloalkyl, aryl, substituted aryl, phenylalkyl or substituted phenylalkyl; and (ii) a chiral phosphine compound of the formula:

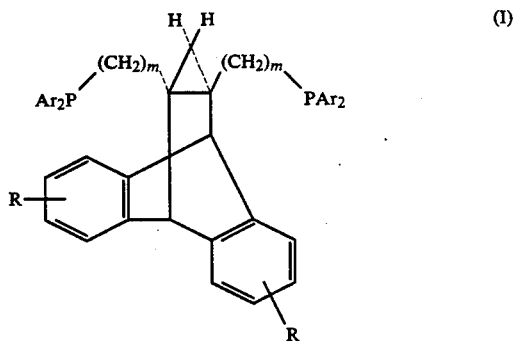

(I)

where R is $C_1$ to $C_6$ linear or branched alkyl, phenyl, substituted phenyl, $C_1$ to $C_6$ linear or branched alkoxy or halo; Ar is phenyl or substituted phenyl or naphthyl or substituted naphthyl; and m is 0 or 1.

2. The process of claim 1 wherein $R_1$ and $R_2$ are the same or different and are hydrogen or alkyl.

3. The process according to claim 2 wherein $R_1$ and $R_2$ are hydrogen.

4. The process according to claim 1 wherein Ar' is phenyl or naphthyl substituted with alkyl or alkoxy.

5. The process according to claim 4 wherein Ar' is phenyl substituted with methyl, ethyl, n-propyl or isobutyl.

6. The process according to claim 1 wherein $R_3$ and $R_4$ are the same and are alkyl.

7. The process according to claim 6 wherein $R_3$ and $R_4$ are methyl.

8. A process for preparing S-ibuprofen which comprises:

(1) catalytically, asymmetrically hydrogenating 2-(4-isobutylphenyl)acrylic acid by utilizing a mixture of:

TABLE

| | | HYGROGENATION RESULTS (900–1000 psi $H_2$) | | | | |
| | Substrate | Catalyst Stoichiometry (mmoles) | | | Temp/Time | Conversion | |
| Example | (mmoles) | Metal Complex | Phosphine Ligand | Solvent | (°C./hr) | (GC Area %) | % ee |
| 1 | UA (1.45)/SS | Ru(acac)$_3$ (0.023) | R-Anthraphos-1 (0.027) | MeOH | 61/7 | 96 | 67 (S) |

I claim:

1. A process for preparing optically active α-aryl aliphatic carboxylic acids which comprises catalytically, asymmetrically hydrogenating an olefinic carboxylic acid of the formula:

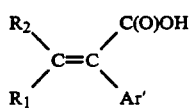

where $R_1$ and $R_2$ are the same or different and are hydrogen, alkyl, cycloalkyl, or haloalkyl; and Ar' is aryl or substituted aryl; by utilizing a mixture of (i) a ruthenium compound of the formula and an optically active anthraphos-m, where $R_3$ and $R_4$ are the same or different and are alkyl and anthraphos-m is:

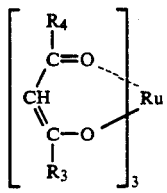

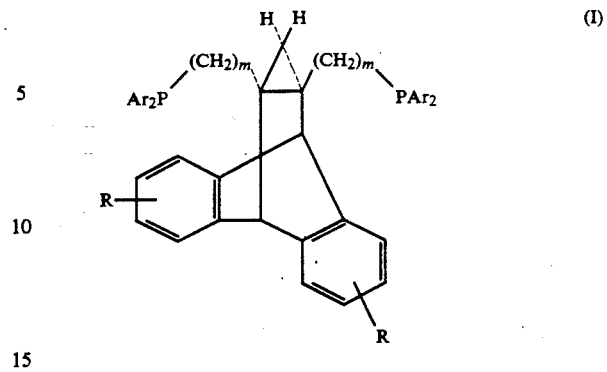

where R is $C_1$ to $C_6$ linear or branched alkyl, phenyl, substituted phenyl, $C_1$ to $C_6$ linear or branched alkoxy or halo; Ar is phenyl or substituted phenyl or naphthyl or substituted naphthyl; and m is 0 or 1; and (2) hydrolyzing the product of step (1).

9. The process of claim 8 wherein $R_1$ and $R_2$ are the same or different and are hydrogen or alkyl.

10. The process according to claim 9 wherein $R_1$ and $R_2$ are hydrogen.

11. The process according to claim 8 wherein Ar' is phenyl or naphthyl substituted with alkyl or alkoxy.

12. The process according to claim 11 wherein Ar' is phenyl substituted with methyl, ethyl, n-propyl or isobutyl.

13. The process according to claim 8 wherein $R_3$ and $R_4$ are the same and are alkyl.

14. The process according to claim 13 wherein $R_3$ and $R_4$ are methyl.

* * * * *